United States Patent [19]

Raemer

[11] Patent Number: 5,365,922
[45] Date of Patent: Nov. 22, 1994

[54] CLOSED-LOOP NON-INVASIVE OXYGEN SATURATION CONTROL SYSTEM

[75] Inventor: Daniel B. Raemer, Brookline, Mass.

[73] Assignee: Brigham and Women's Hospital, Inc., Boston, Mass.

[21] Appl. No.: 671,586

[22] Filed: Mar. 19, 1991

[51] Int. Cl.$^5$ .............................................. A61M 16/00
[52] U.S. Cl. .......................... 128/204.23; 128/202.22; 128/204.21; 128/205.11; 128/205.23
[58] Field of Search ....................... 128/204.18, 204.21, 128/204.23, 716, 719, 202.22, 205.23, 205.11

[56] References Cited

U.S. PATENT DOCUMENTS

| | | | |
|---|---|---|---|
| 2,414,747 | 1/1947 | Kirschbaum | 128/142 |
| 3,734,091 | 5/1973 | Taplin | 128/142 |
| 4,326,513 | 4/1982 | Schulz et al. | 128/203.14 |
| 4,648,397 | 3/1987 | Beale | 128/205.11 |
| 4,665,911 | 5/1987 | Williams et al. | 128/204.21 |
| 4,889,116 | 12/1989 | Taube | 128/204 |
| 5,103,814 | 4/1992 | Maher | 128/205.11 |

FOREIGN PATENT DOCUMENTS

0303502 12/1988 European Pat. Off. .

OTHER PUBLICATIONS

Clement Yu, et al., "Improvement in Arterial Oxygen Control Using Multiple-Model Adaptive Control Procedures," IEEE Transactions on Biomedical Engineering, vol. BME-34, No. 8, Aug. 1987, pp. 567-574.

Adaptive Control of Arterial Oxygen Pressure of Newborn Infants Under Incubator Oxygen Treatments, Sano, A., et al., IEE Proceedings, vol. 132, Pt.D., No. 5, Sep. 1985.

"Dynamic System Identification: Experiment, Design and Data Analysis" by Graham C. Goodwin and Robert L. Payne, Academic Press, New York, 1977.

"Digital Parameter-Adaptive Control of Processes with Unknown Dead Time" by Kurz et al., Automatica, vol. 17, No. 1, pp. 245-252, 1981, Permagon Press.

"The Self-Tuning Controller: Comparison with Human Performance in the Control of Arterial Pressure", Stern et al., Annals of Biomedical Engineering.

*Primary Examiner*—Edgar S. Burr
*Assistant Examiner*—Aaron J. Lewis
*Attorney, Agent, or Firm*—Wolf, Greenfield & Sacks

[57] ABSTRACT

An adaptive controller for delivering a fractional amount of oxygen to a patient. The controller utilizes an oximeter coupled by a non-invasive sensor to the patient for measuring the blood hemoglobin saturation in the patient. The oximeter generates a plurality of blood saturation output signals over a given period of time which are sequentially representative of the patient's blood hemoglobin saturation. A processing means evaluates a plurality of the oximeter output signals and, based on the evaluation, provides a pseudo blood saturation signal. A feedback control means responsive to the pseudo output signal sets the fractional amount of oxygen to be delivered to the patient. When deviations of the oximeter output signal are excessive, the pseudo output signals cause a gradual increase in the fractional amount of oxygen for the patient. Furthermore, the feedback control means is periodically disconnected, and the response of the patient to random changes in the fractional amount of oxygen delivered to the patient is used to adapt the response characteristics of the feedback control means in a manner tailored to the needs of the patient.

28 Claims, 6 Drawing Sheets

CLOSED-LOOP NON-INVASIVE OXYGEN SATURATION CONTROL SYSTEM

BACKGROUND OF THE INVENTION

1. Field of the Invention

The present invention relates to automatic control of blood oxygen saturation ($S_aO_2$) in a patient by adjustment of the fractional amount of oxygen inspired ($FIO_2$) by the patient, and more particularly, to a feedback control loop for a mechanical ventilator including a non-invasive $S_aO_2$ monitor in the feedback path for developing an adaptive control signal which controls the inspired gas blender of the ventilator.

2. Description of the Prior Art

Devices for controlling the oxygen content of the blood by controlling the fraction of oxygen breathed by a patient are well known. For example, U.S. Pat. No. 2,414,747 issued to Harry M. Kirschbaum on Jan. 21, 1947 shows a method and apparatus for controlling the oxygen content of the blood of living animals which discloses control of blood oxygen content by the use of an ear oximeter which produces a signal used to control the proportion of inspired oxygen. As the oximeters direct a beam of light through a capillary bed in the ear, the characteristics of the light become modified by the color of the blood that intercepts its path. Thus, the change in oxygen levels of the blood are detected non-invasively and electrical signals are generated, amplified and used to control the oxygen supply delivered to a patient.

Numerous improvements have been made since that time wherein better matching of oxygen delivery to the needs of the patient have been made such as shown in U.S. Pat. No. 3,734,091 to Ronald H. Taplin issued on May 22, 1973. Taplin discloses an optical oximeter and a temporary oxygen-deficient mixture (anoxic) to control blood oxygen saturation. Thus, to prevent excessive oxygen levels, Taplin discloses limiting the inspired oxygen by intermittently providing the anoxic mixture each time the oxygen saturation of the blood reaches a predetermined percentage level.

U.S. Pat. No. 4,889,116 issued to Taube on Dec. 26, 1989 discloses one type of adaptive controller for adjusting the fraction of oxygen inspired by a patient. The controller utilizes a pulse oximeter connected by an optical sensor to the patient for measuring the patient's blood hemoglobin saturation ($S_pO_2$) and pulse rate. These signals from the oximeter are used by a calculator for determining the fractional amount of oxygen to be inspired by the patient. The calculated percentage of oxygen is provided to the patient so that the gas taken in by the patient automatically causes the blood in the patient to reach a predetermined hemoglobin saturation level in response to the patient's requirements as determined by changes in the $S_pO_2$ signal. However, the calculator is programmed to determine when there is an excess deviation of the patient's pulse rate, thereby indicating patient movement and the probability that the pulse oximeter will provide false $S_pO_2$ values during such patient movement. When an excess deviation in pulse rate is detected, the fractional amount of inspired oxygen is no longer responsive to the measured $S_pO_2$ value, but instead held constant until the excess deviation of the pulse rate has been terminated. Furthermore, a low $S_pO_2$ value, indicative of a depressed respiration (apnea) is also detected, and used to cause a preset higher percentage of inspired oxygen to be supplied to the patient until the depressed respiration of the patient has been terminated. Thus, responsive $FIO_2$ adjustment is suspended during patient movement and apnea, and during this time fixed $FIO_2$ levels are set.

In 1980, H. Katsuya and Y. Sakanashi published an article in the Journal of Clinical Monitoring 1989; 5:82-86 describing a method for evaluating pulmonary gas exchange using a pulse oximeter. They developed the concept of $FI9_x$ (where x is a single digit number) which is the fraction of inspired oxygen necessary to achieve a measured blood oxygen saturation equal to the value of 9x % (e.g. 98%). This experiment was carried out by periodically manually increasing or decreasing the $FIO_2$ control of a gas blender portion of a ventilator until the $S_pO_2$ measurement reached the target percentage (e.g., 98%). The purpose of this experiment was to develop a diagnostic method to evaluate pulmonary gas exchange impairment. A high value of $FI9_x$ was associated with poor pulmonary gas exchange. In this publication, no mention was made of feedback of $S_pO_2$ values for automatic adjustment of $FIO_2$. The present invention recognizes that the pulmonary impairment of a patient can often change during treatment, thereby requiring a change or adaptation of the responsiveness of the $FIO_2$ control loop.

Since adult and neonatal patients in intensive care units suffering from respiratory distress are at risk for developing hypoxemia or oxygen toxicity, certain safety precautions should be taken to prevent $O_2$ under-/overdose. In an attempt to maintain organ normoxia, appropriate clinical care often mandates ventilation with high $FIO_2$, sometimes for several days. Long exposure to high concentrations of oxygen has been implicated in complications including exacerbation of respiratory distress and various central nervous system symptoms. In neonatal patients, oxygen toxicity may result in blindness from retrolentalfibroplasia. Thus, care should be taken to minimize the $FIO_2$ exposure while maintaining adequate $S_pO_2$, so that the onset of these insidious complications can be delayed or avoided. Furthermore, artifacts (false output measurements) are commonly found in the pulse oximeter output due to patient movement and/or low blood perfusion in the area where the patient contacts the pulse oximeter sensor. Additionally, it is difficult to actually know what the arterial blood oxygen saturation percentage is from the $S_pO_2$ (pulse oximeter) measurement. Thus, careful construction of the $S_pO_2$ feedback control system is required.

It is an object of the present invention to provide a method and apparatus which minimizes the $FIO_2$ of a patient while maintaining adequate $S_aO_2$ levels.

It is a further object of the invention to provide artifact rejection processing of the pulse oximeter which is tolerant of the expected false readings of $S_pO_2$, and furthermore, which is adaptive so as to gradually cause the $FIO_2$ to increase as the frequency of the artifacts increases.

It is still a further object of the invention to provide an $FIO_2$ feedback control loop which has a response (transfer characteristic) which is adaptive to the changing requirements of the patient.

It is an even further object of the invention to provide a safety sub-system for the $FIO_2$ control system in order to prevent a failure in the feedback control system from causing injury to the patient due to extremely inappropriate levels of $FIO_2$.

SUMMARY OF THE INVENTION

In accordance with the principles of the present invention, a method and apparatus is provided for evaluating the oximeter $S_pO_2$ measurements for artifact rejection purposes, and furthermore, causing a gradual increase in $FIO_2$ as the frequency of $S_pO_2$ artifacts increases.

In accordance with a further feature of the invention, a safety sub-system is provided which monitors the output signals from various portions of the $FIO_2$ control system for correlation and/or excursion beyond preset threshold values. Signals which exceed the thresholds or which do not correlate, cause safety sub-system to indicate an alarm condition to the physician.

In accordance with further features of the invention, a feedback control means of the $FIO_2$ control loop has an adaptively adjustable response. In the preferred embodiment, the feedback control means comprises a proportional, integral, derivative controller wherein the coefficients of the P, I, D, terms are selectively adjustable in order to provide appropriate respiration therapy to the patient. Additionally, these coefficients may be modified by input signals which are not part of the $FIO_2$ control loop, such as minute ventilation, tidal volume, etc. Finally, the controller response can be adaptive to the needs of the patient, by periodically disabling the controller and monitoring the response of the patient to random fluctuations of $FIO_2$. An evaluation of the response of the patient is used to adapt the response characteristic of the feedback controller.

Other features and advantages of the invention will be apparent from the description of the preferred embodiment and from the claims.

For a fuller understanding of the present invention, reference should now be made to the following detailed description of the preferred embodiment of the invention and to the accompanying drawings.

DETAILED DESCRIPTION OF THE PREFERRED EMBODIMENT

Figure 1:
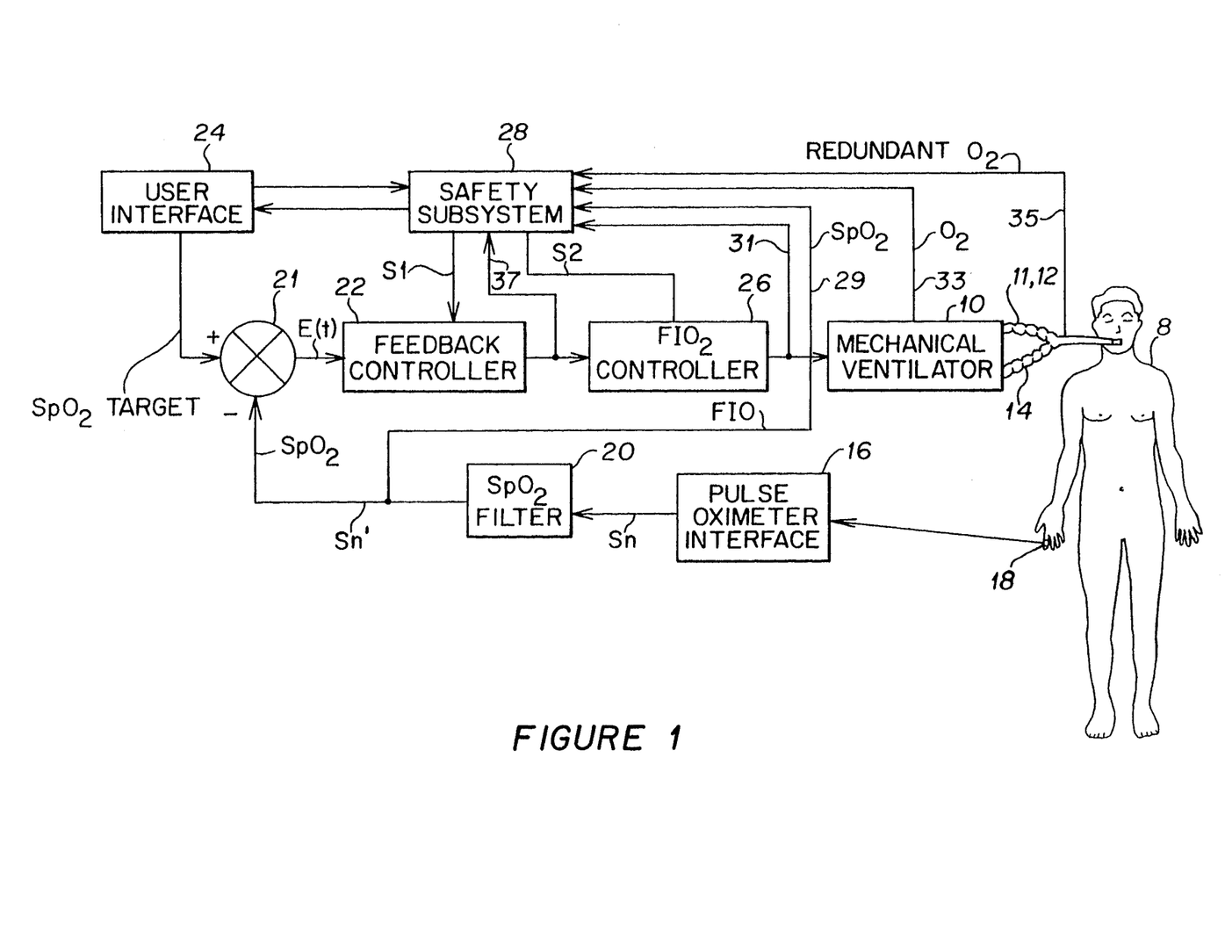
FIG. 1 illustrates a schematic representation of a closed-loop $S_pO_2$ control system constructed in accordance with the present invention for controlling the fractional amount of the inspired oxygen for a patient.

FIG. 1 illustrates in functional block diagram form a preferred embodiment of the present invention. A substantial portion of functions described below are actually carried out by the control system computer, which will be described later on with respect to the user interface. A patient 8 requiring mechanical ventilation is connected to a mechanical ventilator 10 via a breathing circuit 11. Breathing circuit 11 includes an inspiration line 12 by which ventilation gases are unidirectionally delivered to patient 8 and an expiration line 14 for causing unidirectional flow of expired gases from patient 8 to mechanical ventilator 10. Ventilator 10 may comprise any of several well known types of commercially available mechanical ventilators, such as the Model 900C manufactured by Siemens Corporation and available from Siemens Medical Systems, Iselin, N.J. A pulse oximeter 16 of conventional design includes an optical sensor 18 coupled to the finger of patient 8 for non-invasively (e.g., optically) providing a measurement $S_pO_2$, in a well known manner, of the blood oxygen saturation level of patient 8. Pulse oximeter 16 may be, for example, of the type manufactured by Siemens Corporation and comprise the Model 961 monitor system including a pulse oximeter cartridge unit therein. Pulse oximeter 16 includes an output for providing a high speed serial digital signal output $S_pO_2$ representative of the measured $S_aO_2$ level.

Before the measured $S_pO_2$ level can be used for controlling the $FIO_2$, certain precautions must be taken. The present inventor has recognized the importance of providing artifact rejection filtering techniques to the measured $S_pO_2$ level, in order to prevent erroneous operation of the $FIO_2$ feedback control system. That is, it is normal during the operation of a pulse oximeter, that artifact (false) output information will occasionally be generated in response to e.g., physical movement of patient 8 and/or low profusion in the area of sensor 18. This factor was noted in the forenoted Taube patent, however, responsive $FIO_2$ control was suspended during patient movement. However, in the present invention, an $S_pO_2$ artifact filter 20 is provided for processing the output of pulse oximeter 16. In the preferred embodiment, the function of filter 20 is provided completely by software processing in the control system microprocessor. An algorithm is used which rejects artifactual measurements of $S_pO_2$ based on the statistics of past measurements of $S_pO_2$. The algorithm replaces measured values of $S_pO_2$ which fall substantially outside the variance of previous values of $S_pO_2$ with pseudo values. These pseudo values are related to the average $S_pO_2$ values and, in accordance with a further aspect of the present invention, the frequency of the artifactual $S_pO_2$ values. As the frequency of artifacts increases the pseudo values are made increasingly less than the mean value, thereby causing the $FIO_2$ to be gradually increased. Thus, the algorithm provides an adaptive filtering of the $S_pO_2$ values and gradual increase in the $FIO_2$, based on the frequency of the detected artifacts. Details of filter 20 will be described later on in conjunction with FIG. 2.

After appropriate artifact rejection filtering, the $S_pO_2$ value is then compared with a target $S_pO_2$ value in a comparator 21 and the difference signal E(t) (error) is then applied to a feedback controller module 22. The target $S_pO_2$ value is provided by a user interface 24 which may comprise a personal computer of conventional design programmed in the C software language and which includes a keyboard, display, microprocessor and data storage means. The system user will input, via the keyboard, the desired set-point and limit values for the blood oxygen saturation levels as well as other patient data. The user interface display provides data to the physician informing him/her of the status of the system, the $S_pO_2$ set-point, the measured $S_pO_2$ and the measured $FIO_2$.

Feedback controller 22 may comprise a PID (Proportional-Integral-Derivative) controller, such as described in greater detail later on. Feedback controller 22 receives the error signal provided by comparator 21 and produces a stable control signal in response thereto, having a zero steady state error and limited overshoot. In a preferred embodiment of the invention, the proportional, integral and/or derivative terms are selectively controllable for adapting the response of controller 22. Feedback controller 22 is also adaptive as a function of external input signals, such as minute ventilation (the amount of gas breathed by a patient in one minute). Additional novel features of feedback controller 22 will also be described later on relating to the periodic introduction of random $FIO_2$ level changes, which are used to adapt the response of the feedback compensation. Feedback controller 22 provides an output which indicates what the $FIO_2$ level should be, e.g., 30%.

An $FIO_2$ controller 26, comprised partly of software and partly of hardware including a stepper motor, calculates the present set-point of the $FIO_2$ being delivered to the patient, compares this with the instructions received from feedback controller 22, and then mechanically controls a gas blender included in mechanical ventilator 10 for causing the $FIO_2$ level to be adjusted. The gas blender, not specifically shown, is a conventional part added to or built-in to mechanical ventilator 10 which controls the mixing of gas from an air source and an $O_2$ source, respectively, to the gas input of ventilator 10. For example, assume that feedback controller 22 provides an output (in software) to $FIO_2$ controller 26 demanding that the $FIO_2$ be increased to 30%. The software portion of $FIO_2$ controller 26 will then calculate a number of pulses, e.g., 30 to the right, that must be applied to the stepper motor in order to cause the gas blender of mechanical ventilator 10 to cause a 30% mixture between $O_2$ and air. This mechanical connection is indicated by the output from controller 26 to mechanical ventilator 10, although an electronic control could also be used.

A final portion of the invention comprises safety sub-system 28. A series of safety features are implemented in hardware and software which comprise safety sub-system 28 to prevent hypoxic inspired mixtures and inadvertent errors in the operation of the $FIO_2$ control system. These include:

1. Limit (threshold) values of $S_pO_2$ and $FIO_2$ are entered into the system by the user via interface 24. Safety sub-system 28 monitors the artifact corrected $S_pO_2$ value via line 29, the $FIO_2$ output from controller 26 via line 31, and the actual $O_2$ level sensed in ventilator 10 and inspiration line 12 via lines 33 and 35, respectively. Excursions beyond the pre-set thresholds are detected by sub-system 28 and cause visual and audible alerts to be directed to the physician.

2. The system resets (see 4 below) based on missing signals from pulse oximeter 16 or ventilator 10.

3. The system detects error between desired $FIO_2$ (i.e., the output from controller 22 via line 37) and the measured $FIO_2$ at three different places. The first place is the output of controller 26 via line 31, the second place is the $O_2$ indication signal which is provided from mechanical ventilator 10, via line 33 and the third place is a redundant $O_2$ indication signal provided from an $O_2$ sensor in breathing circuit 11, via line 35. Each of these values should be correlated; if not, an alarm condition is indicated.

4. The system automatically sets the output of controllers 22 and 26 to 100% when any of the above signals indicate error, via set lines S1 and S2 which are coupled to controllers 22 and 26, respectively, from safety sub-system 28.

5. All data is stored on magnetic media for retrospective analysis.

Next, details of artifact filter 20 will be described in conjunction with FIG. 2. This filter algorithm is intended to handle artifacts in a safe, i.e. conservative, manner. Firstly, it recognizes that the pulse oximeter is artifact prone because it is sensitive to both patient movement and blood perfusion in the area of sensor 18. Secondly, it assumes that when data is missing or suspiciously different (e.g., low) compared to the date immediately preceding it, it is probably artifactual. When artifacts are occurring, the worst scenario is that the $S_pO_2$ is actually falling, and increasing the patient $FIO_2$ would be the appropriate therapy. Thus, when artifacts are occurring, we want to balance our concern that the $S_pO_2$ may be falling with the knowledge that missing data is a routine occurrence. Furthermore, as the frequency of missing data increases, our concern that $S_pO_2$ might be falling should also increase. Thus, in accordance with a further aspect of the present invention, when $S_pO_2$ data is missing or suspiciously low (e.g., more than two standard deviations away from the mean of the previous values) we will initially assume the true $S_pO_2$ value is likely to be the mean value. Additionally, in accordance with still a further aspect of the invention, to be conservative we will subtract an adaptive factor from the mean value to recognize the potential that the actual $S_pO_2$ value may be falling. The factor is adaptively increased as the frequency of occurrence of the artifacts increases. This results in progressively increasing levels of $FIO_2$ for the patient to be set by the $FIO_2$ control system.

The artifact rejection algorithm of filter 20 is designed to insure that the $FIO_2$ control system operates normally. As artifacts occur, the control system will tend to increase $FIO_2$ gradually. Thus, as the frequency of artifacts increases, the controller will drive $FIO_2$ up harder. When the frequency of occurrence of the artifacts exceeds an intolerable limit, an alarm will sound and the controller will go open loop with $FIO_2 = 100\%$.

Figure 2:
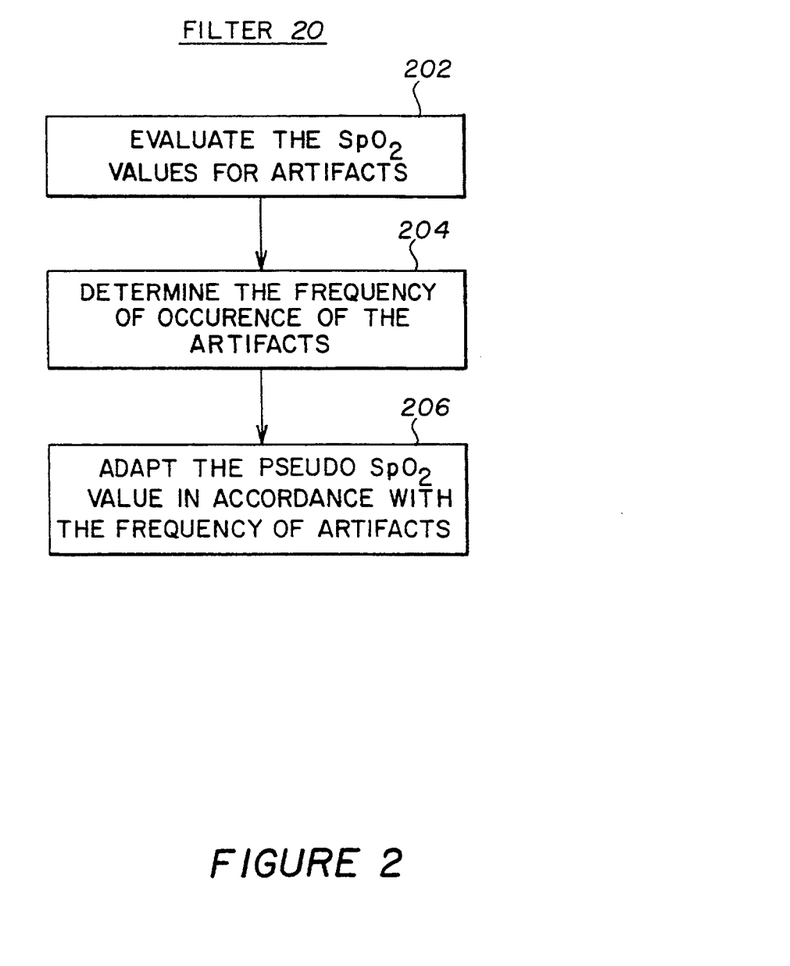
FIG. 2 is a block diagram of the flow control algorithm used for artifact rejection in the output signal from the pulse oximeter shown in FIG. 1.

As shown in FIG. 2, filter 20 operates in accordance with the following process:

Step 202: Evaluate the $S_pO_2$ values for artifacts,
Step 204: Determine the frequency of occurrence for the artifacts, and
Step 206: Adapt the pseudo $S_pO_2$ control value in accordance with the artifact occurrence frequency.

This process is accomplished as follows:

Step 202

As shown in FIG. 1, $S_n$ = current $S_pO_2$ value from pulse oximeter 16. $S'_n = S_pO_2$ value sent to comparator 21.

$S_{n-m}, \ldots, S_{n-3}, S_{n-2}, S_{n-1}, S_n$ is a series of m past $S_pO_2$ output values.

Compute a running average of $S_{n-m}$ as:

$$\overline{S_n} = \left( \sum_{i=n-m}^{n-1} S_i \right) \div m$$

-continued

Compute a standard deviation of $S_{n-m}$ as:

$$\hat{S}_n = \left( \frac{\sum_{i=n-m}^{n-1} (S_i)^2 - \left(\left(\sum_{i=n-m}^{n-1} S_i\right)^2\right) \div m}{m-1} \right)^{\frac{1}{2}}$$

Then, let $M_n$=a binary logical variable (possible artifact). We then set up four tests (windows) to determine if $M_n$ is TRUE, i.e., an artifact, or FALSE, i.e., probably not an artifact but a good $S_pO_2$ value from oximeter 16.

1. If $S_n < (\bar{S}_n - 2\hat{S}_n)$ and $\hat{S}_n > 2$ then $M_n$=TRUE
2. If $S_n < (\bar{S}_n - 4)$ and $\hat{S}_n \leq 2$ then $M_n$=TRUE
3. If $S_n \geq (\bar{S}_n - 2\hat{S}_n)$ and $s_n > 2$ then $M_n$=FALSE
4. If $S_n \geq (\bar{S}_n - 4)$ and $\hat{S}_n \leq 2$ then $M_n$=FALSE As you can see from tests 1 and 3, if the standard deviation is greater than 2, it is relatively safe to say that if SN has a value which less than and due two standard deviations below the running average value, it's probably artifactual, and if $S_n$ is not less than two standard deviations from the running average, it's probably valid. For example, if the running average=96% and the standard deviation is 3%, if the current $S_n$ is less than 90%, it's assumed to be an artifact and if equal to or greater than 90%, it is assumed to be valid.

Tests 2 and 4 are intended for the case where the standard deviation is small, i.e. less than or equal to 2%. Under these circumstances it would be difficult to use standard deviation as a measure of validity since even slight changes can be erroneously considered artifacts. Thus, under these circumstances, a fixed change in $S_n$ from the running average is used as the validating criteria. In the preferred embodiment, the fixed amount is a 4% change. For example, if the running average was 96% and the current $S_n$ was 93%, it would not be considered an artifact. It should be understood that the criteria given here are those currently being used by the inventor, and that future testing may result in modifications of these values and even the use of other criteria, such as the average absolute difference of each value from the mean value.

Step 204

Compute the frequency of artifact occurrences $$F_n = \frac{\text{number of TRUE } M's}{m},$$

for $M_i$ where $i=M-m$ to $n-1$

Step 206

1. If $M_n$=FALSE then $S'_n = S_n$
2. If $M_n$=TRUE then $S'_n = S_n - Q$, where Q is one of $q_1$, $q_2$ or $q_3$.
Where,
$Q=q_1$ if $1/m < F_n \leq f_a$;
$Q=q_2$ if $f_a < F_n \leq f_b$; and
$Q=q_3$ if $f_b < F_n \leq f_c$.
Also:
3. If $F_n > f_c$ then: a) ALARM, b) set FIO2=100%; and c) set $S'_n = 0.5\%$ (an arbitrary small, non-zero amount)
4. If $\bar{S}_n > \frac{1}{3} \hat{S}_n$ then ALARM In the preferred embodiment, m=10 sample $S_pO_a$ values, $f_a$3/10, $f_b$=5/10, $f_c$=6/10, and $q_1$=0.5%, $q_2$=1.0%, and $q_3$=2.0%.

Feedback controller 22 of the present invention is of the PID (Proportional-Integral-Derivative) controller type, and computes a feedback compensation response which is related to the difference between the desired (set-point) and measured $S_pO_2$ values i.e., the output of comparator 21. The flow of the $O_2$ gas which is added to the breathing mixture of the patient is controlled by an electronic signal from controller 22 which is used to adjust the stepper motor of controller 26. The electronic signal is a function of the sum of three terms:

$$Y(t) = C_1 \cdot E(t) + C_2 \int E(t)dt + C_3 \frac{dE(t)}{dt}$$

where Y(t) is the flow control signal, $C_1$, $C_2$ and $C_3$ are constants E(t) is the Error (difference between the desired $S_pO_2$ and the measured $S_pO_2$ ($S'_n$) and dE(t)/dt is the time derivative of E(t). The output Y(t) may be adjusted by a constant of proportionality as circumstance may dictate.

Figure 3:
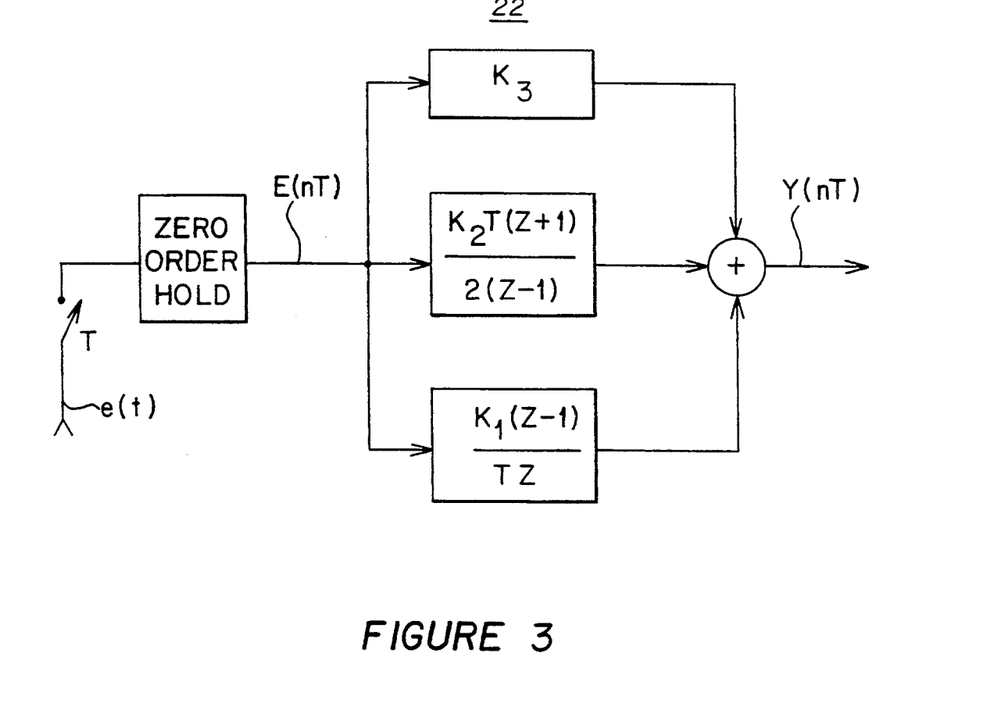
FIG. 3 is a block diagram of a digital PID controller used in the feedback control system of the present invention.

Although the above is an analog implementation of feedback controller 22, it is also possible to use a sampled-data equivalent feedback controller, such as commonly used with microcomputers. The block diagram of a digital PID controller of the preferred embodiment is shown in FIG. 3. The transfer function of the digital PID controller is as follows:

$$\frac{Y(nT)}{E(nT)} = K_3 + \frac{K_2 T(Z+1)}{2(Z-1)} + \frac{K_1(Z-1)}{TZ}$$

The microcomputer of the user interface system samples the input variable (E(t))periodically (every T seconds). Computer software is used to mathematically implement the feedback algorithm of controller 22.

While the output of the digital controller is presented every T seconds, a circuit element called a zero-order-hold takes the periodically produced output e(t), holds it steady and implements the controlling output action.

In the block diagram of the digital PID controller in FIG. 3, $K_3$, $K_2$ and $K_1$ are coefficients (gain constants) of the proportional, integral and derivative terms, respectively. T is the sample time interval, n is an integer number of sample intervals. Z is the Z-transform operator, E(nT) is the error signal e(t) sampled every T seconds, and Y(nT) is the desired FIO2 value Note that $K_3$, $K_2$ and $K_1$ serve the same purpose as $C_1$, $C_2$ and $C_3$ in the analog implementation discussed previously; however, the values of $K_1$, $K_2$ and $K_3$ may be different from $C_1$, $C_2$ and $C_3$.

Figure 4:
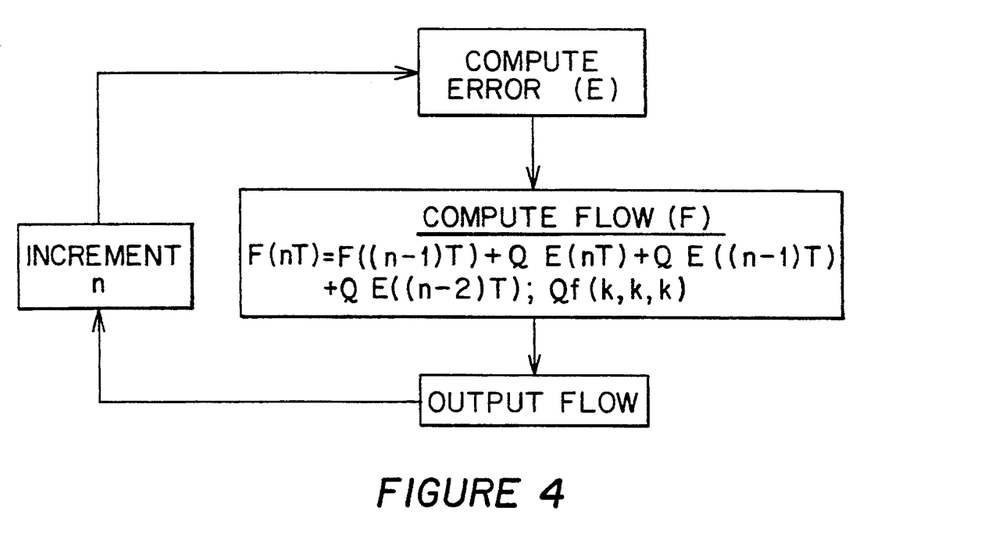
FIG. 4 is a block diagram of the computational process of the PID controller of FIG. 3.

A block diagram of this process is shown in FIG. 4. The values of the coefficients as shown in FIG. 4 are dependent on the characteristics of the design of the system which is being controlled. The increment (n), error (E), flow (F) and the output are functions of the volume and flow characteristics of the breathing circuit, the patient's lung and $O_2$ transfer characteristics, and the settings of the ventilator.

It is also possible to use the patient's minute ventilation (MV), title volume (TV), and/or respiratory rate (RR) to modify one or more of the terms in the above circuit equation. The patient's minute ventilation, tidal volume, or respiratory rate may be measured using any of several well-known techniques. For example, these measurements may be based on thermal dissipation, a pressure difference across a resistive element (pneumotachograph), the rotation rate of a vane, or the oscillation frequency of a fluid vortex. This type of modification of the invention will be described next in greater detail with respect to FIG. 6. Furthermore, in accordance with another aspect of the invention, design goals such as tolerable overshoot, time to achieve control and accuracy of control are also used to determine the value of coefficients $K_1$, $K_2$ and $K_3$. Details relating to modifications of this type are described in greater detail with respect to FIG. 7.

First, however, the initial set-up of controller 22 will be described. Referring to the above equation for the transfer function of the digital PID controller, the values of $K_1$, $K_2$ or $K_3$, or any selective combination of $K_1$, $K_2$ and $K_3$ are adjusted as a function of the error signal e(t), i.e., the output of comparator 21. The initial set-up of these values is accomplished in order to tailor the response of the $FIO_2$ control system in accordance with the clinical goals for given classes of patients. For example, there may be a first set of values for $K_1$, $K_2$, $K_3$ for adults and a second set of K values for neonatal. patients.

Figure 5A:
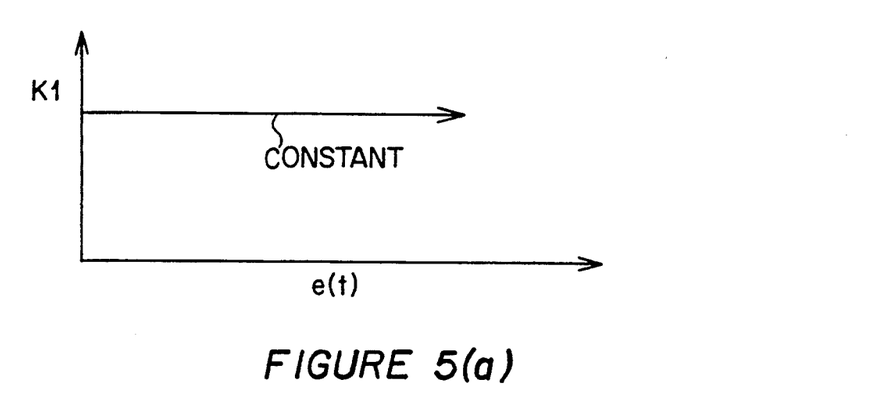
FIGS. 5(a) to 5(c) are graphical representations of the non-linear operation of the PID controller of FIG. 3.

In accordance with a further aspect of the invention, these K values of the PID controller are made non-linear in order to more appropriately tailor the response of the $FIO_2$ system in accordance with empirically determined desired values for specific classes of patients. Additionally, it is noted that the non-linear gain provided by PID controller 22 makes the response of the $FIO_2$ control loop more clinically appropriate. For example, FIG. 5(a) illustrates a value for $K_1$ as a function of e(t). However, a limiting value is provided so that the integrator term does not get to large. Although the previously noted U.S. Pat. No. 4,889,116 to Taube includes a PID controller, it is noted that no individual control of the proportional or integral or derivative terms is provided, such as specifically provided by the present invention.

Figure 5B:
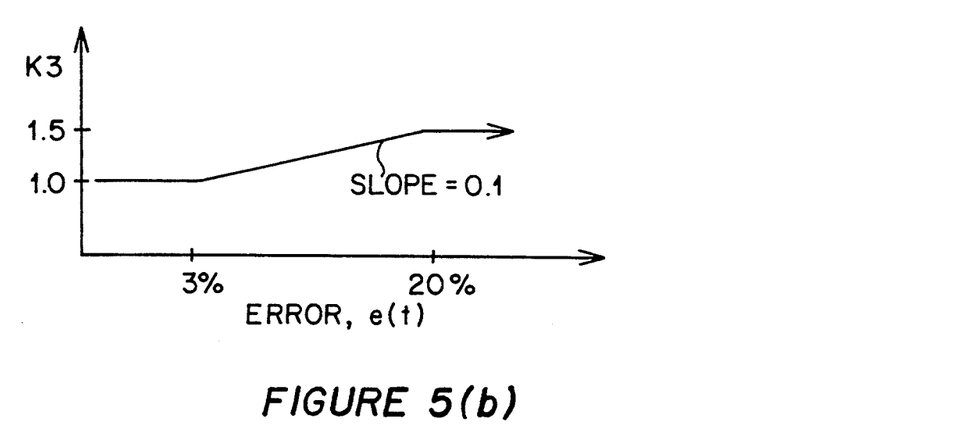
Figure 5C:
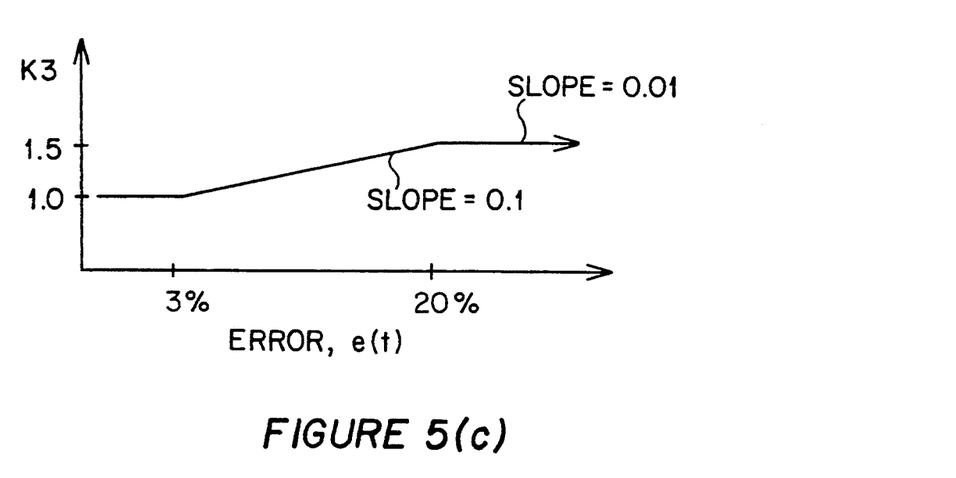

FIG. 5(b) illustrates an additional non-linear characteristics for the K values, which was used for the $K_3$ value specifically in the preferred embodiment of the present invention and FIG. 5(c) is an alternative embodiment thereof. Thus, it is apparent from these figures that non-linear coefficients are provided for various ones of the terms of the PID controller which change in real time in accordance with the error signal provided at the output of comparator 21.

Additionally, it is noted that limiting values are also imposed upon the output of PID controller, as previously noted, which prevent the output $FIO_2$ values from being greater than 100% or less than 0%.

Figure 6A:
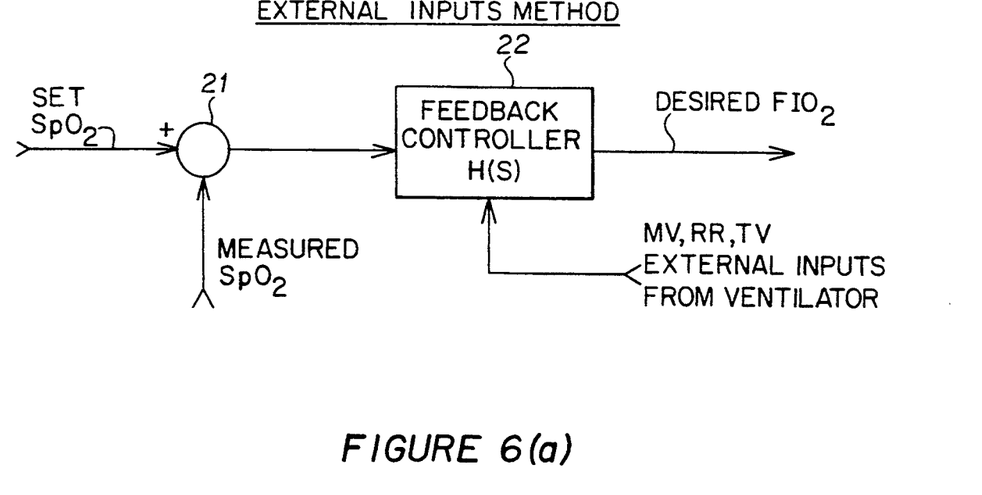
FIG. 6(a) illustrates a block diagram of the PID controller transfer function in the Laplace domain and FIG. 6(b) illustrates a range of values for K3, a term in the controller transfer function.
Figure 6B:
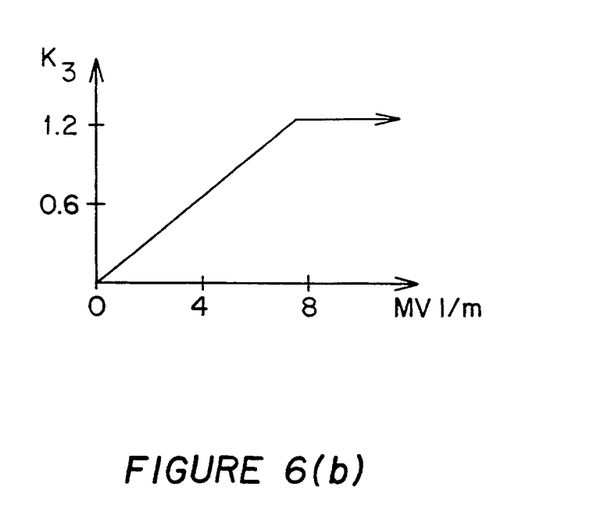

FIG. 6(a) is illustrative of the way in which external inputs can be applied to control the coefficients of PID controller 22 in order to change the system response accordingly. The external inputs may comprise the minute ventilation (MV), the respiratory rate (RR) and/or the tidal volume (TV). For example, $K_1$ could be a function of minute ventilation or $K_1$, $K_2$, $K_3$ could be functions of RR, MV and TV, respectively. In fact, any combination of functional relationships between the K's and external inputs are possible. In the preferred embodiment, the value of $K_3$ is changed in response to the minute ventilation as shown in FIG. 6(b).

A final control of the characteristics for controller 22 relates to an adaptiveness of its response to the changing needs of the patient. In this regard, it is noted that in the forenoted Taube U.S. Pat. No. 4,889,116, the controller program described in Exhibit A initially asks the user to input a "lung time constant tl". The present inventor has recognized that the initial values of k which determine the controller response may not be appropriate during later periods of the ventilation therapy for the patient. In accordance with a further feature of the invention, the PID controller output is periodically and randomly varied (within prescribed safety limits) in order to adapt the responsiveness of controller 22 with the changing needs of the patient.

Figure 7A:
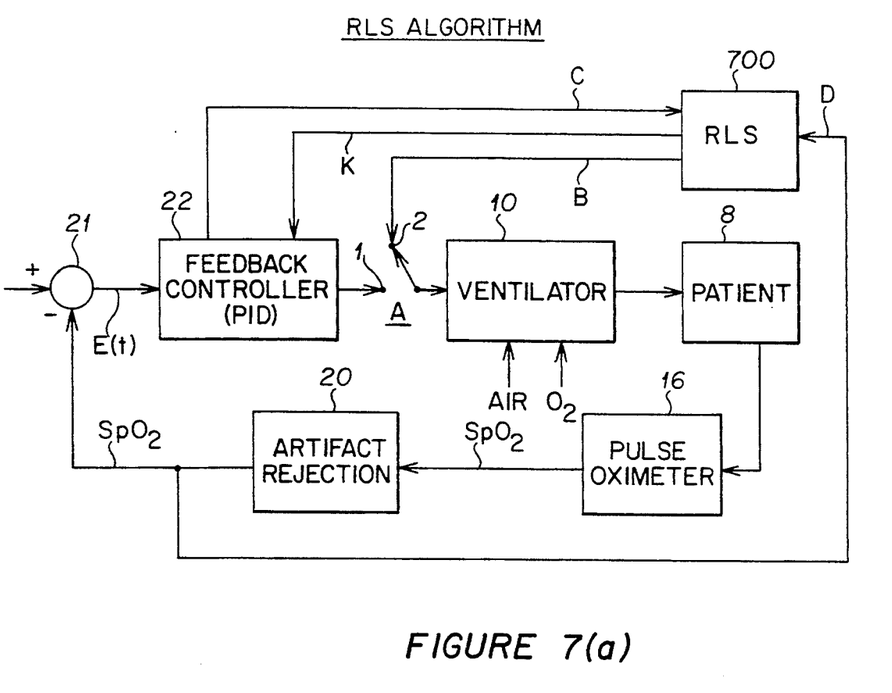
FIGS. 7(a) and (b) illustrate a block diagram and waveform useful for understanding the RLS method.

FIG. 7(a) illustrates a functional block diagram of the $FIO_2$ control loop including a Recursive Least Squares (RLS) computation used for modifying the response of controller 22. When software switch A is in position one, the RLS algorithm 700 is dormant. Under these conditions, the values for the gains of the PID feedback compensation ($K_1$, $K_2$ and $K_3$) are set at their initial (default) values.

When RLS algorithm 700 is activated, switch A is in position two, and a sequence of random magnitude $FIO_2$ values are applied to the blender of ventilator 10 via line B. The sequence of random $FIO_2$ values are a percentage ($\pm$) of a predetermined $FIO_2$ value. The predetermined value is the last value of $FIO_2$ before the RLS algorithm was started (which is input to RLS algorithm 700 via line C). The initial value may also be an average of several previous $FIO_2$ values in order to eliminate the possibility that the last $FIO_2$ value is non-representative of the actual needs of the patient.

Figure 7B:
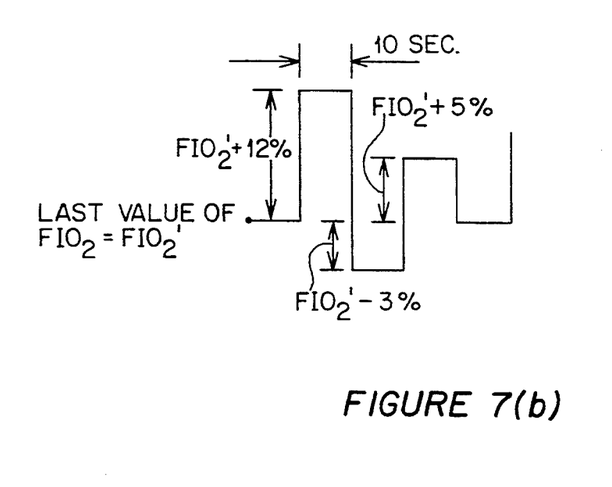

FIG. 7(b) illustrates an example of what one such random sequence might look like. The random 10 second periods of $FIO_2$ $\pm m$ % occur approximately 20 to 60 times each 15 minutes, in the preferred embodiment. The range of amplitudes of m is set by clinical considerations and performance issues. A range of m equal to 10%, 15% and 20% has been used.

The response of the patient as measured by pulse oximeter 16 is input to RLS algorithm 700 via line D for processing. When the RLS algorithm has collected several values, in the preferred embodiment 30, it begins to process these values in accordance with the Recursive Least Squares (RLS) computation, such as known by those skilled in the art, and described for example in "Dynamic System Identification: Experiment, Design and Data Analysis" by Graham C. Goodwin and Robert L. Payne, Academic Press, New York, 1977; and an article entitled "Digital Parameter-Adaptive Control of Processes with Unknown Dead Time" by Kurz et al. in Automatica, Vol. 17, No. 1, pp. 245–252, 1981, published by Permagon Press; and as also described in conjunction with control of arterial blood pressure in an article entitled "The Self-Tuning Controller: Comparison with Human Performance in the Control of Arterial Pressure" by Kenneth S. Stern et. al., published in the Annals of Biomedical Engineering.

Briefly, what the RLS algorithm does is find a set of coefficients (a's and b's) of a linear combination of past and present $FIO_2$ values and past $S_pO_2$ values for determining an estimated $S_pO_2$ value, which set of coefficients minimizes the mean square difference between this estimated value of $S_pO_2$ and the actually measured value of $S_pO_2$. When values for a and b are obtained which cause the computed and measured values to be substantially equal, it can be said that the RLS algorithm has converged. If 30 samples of $S_pO_2$ at 10 second intervals was not enough to cause convergence, the RLS algorithm will continue acquiring new $S_pO_2$ values while dropping the oldest $S_pO_2$ values and then try to converge. Upon convergence, new values may be found for the time constant (T) and time delay (L) of the controller response, which leads to new values for the $K_1$, $K_2$, and $K_3$, coefficients, respectively. These new coefficients are coupled to controller 22 via line K.

Thus, there has been shown and described a novel method and apparatus for controlling the amount of oxygen inspired by a patient. Many changes, modifications, variations and other uses and applications of the subject invention will, however, become apparent to those skilled in the art after considering this specification and the accompanying drawings, which disclose a preferred embodiment thereof. For example, the PID controller of the present invention could in fact be a PI controller or! some other type of controller having adjustable response characteristics. Furthermore the feedback control loop could be integrated into the ventilator 10 or pulse oximeter 16. All such changes, modifications, variations and other uses and applications of the invention are deemed to be covered by the claims which follow.

What I claim is:

1. An adaptive controller for delivering a fractional amount of oxygen to a patient, said controller comprising:
   oximeter means coupled by a non-invasive sensor to said patient for measuring blood hemoglobin saturation in the patient, said oximeter generating a plurality of blood hemoglobin saturation output signal values over a given period of time, sequentially representative of said blood hemoglobin saturation;
   means for generating a running average of said blood hemoglobin saturation output values;
   means for generating pseudo-output signals that are a function of said running average;
   processing means including means for identifying possibly invalid output signal values and being responsive to said blood hemoglobin saturation output signal values for evaluating a plurality of said blood hemoglobin saturation output signal values and, based on said evaluation, providing a processed output signal;
   means for substituting respective pseudo-output signals for each of said possibly invalid output signal values thereby forming a sequence of valid output signals.

2. The adaptive controller of claim 1 wherein said oximeter is a pulse oximeter and said plurality of blood hemoglobin saturation output signal values are oxygen saturation of hemoglobin values as measured by a pulse oximeter ($S_pO_2$ values).

3. The adaptive controller of claim 1 wherein said processing means includes:
   artifact recognition means for identifying possibly invalid output signal values and for providing a sequence of valid output signal values, exclusive of said identified possibly invalid output signal values; and
   means for generating a running average of said sequence of valid output signal values and for providing said running average as said processed output signal.

4. The adaptive controller of claim 3 wherein said artifact recognition means includes means for comparing each of said plurality of output signal values to said running average and for identifying as possibly invalid any output signal value which differs from said running average by more than a predetermined amount.

5. The adaptive controller of claim 3 wherein said means for generating said running average includes means for calculating a mean value and a standard deviation value for m of said plurality of valid output signal values most recently provided by said artifact recognition means, where m is an integer, and for providing said calculated mean value as said processed output signal.

6. The adaptive controller of claim 5 wherein said artifact recognition means includes means for comparing each of said plurality of output signal values to said mean value and for identifying as possibly invalid any output signal value which differs from said mean value by an amount greater than two time said standard deviation value.

7. The adaptive controller of claim 5 wherein the feedback control means includes:
   means for generating a difference signal having a value which represents the difference between the processed output signal and a value representing a desired blood hemoglobin saturation value; and
   means, responsive to said difference signal, for changing the fractional amount of oxygen delivered to the patient in a sense which tends to reduce the value of said difference signal.

8. The adaptive controller of claim 7 wherein the means for changing the fractional amount of oxygen delivered to the patient includes a proportional-integral-derivative controller.

9. An adaptive controller for delivering a fractional amount of oxygen to a patient, said controller comprising:
   oximeter means coupled by a non-invasive sensor to said patient for measuring blood hemoglobin saturation in the patient, said oximeter generating a plurality of blood saturation output signal values over a given period of time, sequentially representative of said blood hemoglobin saturation;
   processing means responsive to said blood saturation output signal values for evaluating a plurality of said output signal values and, based on said evaluation, providing a processed output signal; and
   feedback control means continuously responsive over a full range of patient activity to said processed output signal for determining the fractional amount of oxygen to be delivered to the patient;
   wherein the processing means includes:
      artifact recognition means for identifying possibly invalid output signals values and for providing a sequence of valid output signal values, exclusive of said identified possibly invalid output signal values; and
      means for generating a running average of valid output signal values and for providing said running average as said processed output signal; and
   wherein the artifact recognition means further includes means for substituting respective pseudo output signal values for each of said identified possibly invalid output signal values to generate said sequence of valid output signal values, wherein the value of said pseudo output signal values is a function of said running average of said oximeter means output signal values.

10. The adaptive controller of claim 9 wherein said processing means further includes:

monitoring means, coupled to said artifact recognition means, for determining the frequency of occurrence of said possibly invalid output signal values; and means, coupled to said monitoring means, for decreasing the value of said pseudo output signal values in proportion to the frequency of occurrence of said possibly invalid output signal values to condition the feedback control means to gradually increase the fractional amount of oxygen to be delivered to the patient.

11. An adaptive controller for delivering a fractional amount of oxygen to a patient, said controller comprising:

measuring means, coupled to the patient, for measuring blood oxygen level in the patient and for providing a plurality of output signal values, sequentially representative of said measured blood oxygen level;

processing means, coupled to said measuring means, for generating a running average of said plurality of output signal values and for subtracting said running average from a target value, representing a desired blood oxygen level for the patient, to produce a difference signal;

feedback control means, coupled to receive said difference signal, for adjusting the fractional amount of oxygen to be delivered to the patient to minimize said difference signal in magnitude.

12. An adaptive controller for delivering a fractional amount of oxygen to a patient, said controller comprising:

measuring means, adapted to be coupled to the patient, for measuring blood oxygen level in the patient and for providing a plurality of output signal values, sequentially representative of said measured blood oxygen level;

processing means, coupled to said measuring means, for generating a running average of said plurality of output signal values and for subtracting said running average from a target value, representing a desired blood oxygen level for the patient, to produce a difference signal;

feedback control means, coupled to receive said difference signal, for adjusting the fractional amount of oxygen to be delivered to the patient to minimize said difference signal in magnitude;

wherein the feedback controller is defined by a transfer function, having a plurality of adjustable coefficients, which establishes how the fractional amount of oxygen delivered to the patient is to be changed, both in time and in magnitude, in response to a change in the difference signal.

13. The adaptive controller of claim 12, further including:

means for measuring a plurality of physiological parameters related to respiration to produce a respective plurality of output signals; and adjustment means responsive to said plurality of output signals for adaptively changing the values of said coefficient values to change the transfer function of said feedback controller.

14. The adaptive controller of claim 13 wherein said physiological parameters include one or more of minute ventilation, respiratory rate and tidal volume; and said adjustment means includes means for automatically adjusting said coefficient values as a function of said plurality of output signal.

15. The adaptive controller of claim 12 further including means for periodically and automatically varying the coefficient values to change the transfer function of the feedback controller to track changing needs of the patient.

16. the adaptive controller of claim 15 wherein the means for periodically and automatically varying the coefficient values includes:

means for randomly changing the fractional amount of oxygen to be delivered to the patient within predetermined minimum and maximum limiting values; and coefficient adapting means, responsive to the respective measured blood oxygen level values resulting from the changes in the fractional amount of oxygen, for adjusting the coefficient values to match the response of the control system to the response of the patient.

17. The adaptive controller of claim 16 wherein the coefficient adapting means includes:

means for recording the random sequence of changes in fractional amount of oxygen delivered to the patient and the respective measured blood oxygen levels resulting from the sequence of changes in the fractional amount of oxygen;

means for calculating, based on the recorded changes in the fractional amount of oxygen, the recorded blood oxygen levels and the transfer function of the feedback controller, an expected present blood oxygen level; and means for repeatedly changing the coefficient values and recalculating the expected present blood oxygen level to minimize any difference in magnitude between the expected present blood oxygen level and the measured blood oxygen level currently provided by the measuring means.

18. The adaptive controller of claim 17 wherein the means for repeatedly changing the coefficient values includes means for evaluating the recorded changes in the fractional amount of oxygen, the recorded blood oxygen levels and the transfer function of the feedback controller according to a recursive least squares optimization method.

19. The adaptive controller of claim 12 wherein the feedback controller is a proportional-integral-derivative (PID) controller.

20. The adaptive controller of claim 19 wherein the transfer function, Y(nT)/E(nT), defining the feedback controller is given by an equation:

$$Y(nT)/E(nT) = K_3 + K_2 T(Z+1)/(2(Z-1)) + K_1(Z-1)/(TZ)$$

where $K_3$, $K_2$ and $K_1$ are respective proportional, integral and derivative coefficient values, Z is the Z-transform operator, T is a sampling interval in seconds, n is the number of current sample values, Y(nT) is the current output value and E(nT) is the current value of the difference signal.

21. In a system for automatically providing a controlled fractional amount of oxygen to a patient, including an oximeter for measuring blood oxygen levels of the patient and a feedback controller, coupled to the oximeter for adjusting the fractional amount of oxygen delivered to the patient to maintain the measured blood oxygen levels within predetermined limits, a safety subsystem to prevent the system from erroneously administering a hypoxic mixture, said safety subsystem comprising:

means for measuring the fractional amount of oxygen being delivered to the patient and for providing a signal indicative thereof including means for sensing the oxygen level of the air being provided to the patient using a plurality of sensors;

means for correlating the measured fractional amount of oxygen to a preferred fractional amount of oxygen as determined by the feedback control system and for providing an alarm signal when the measured and preferred fractional amounts of oxygen are determined to be uncorrelated including means for correlating the preferred fractional amount of oxygen to each of the plurality of sensed oxygen levels and for generating said alarm signal if any of the sensed oxygen levels is not correlated to said preferred fractional amount of oxygen; and means, responsive to said alarm signal, for adjusting the fractional amount of oxygen to be delivered to the patient to a maximum value said safety subsystem further including means for monitoring the blood oxygen level signals provided by the oximeter including means to identify possibly invalid signal values and means to provide a sequence of valid signal values, exclusive of said identified possibly invalid signal values; and said safety subsystem includes means for setting a first threshold value representing a minimum desirable level of said blood oxygen level signal and a second threshold value representing a minimum desirable level of said preferred fractional amount of oxygen and said measured fractional amount of oxygen; and means for producing said alarm signal when one of said sequence of valid signal values is less than said first threshold value; means for producing said alarm signal when one of said preferred fractional amount of oxygen and said measured fractional amount of oxygen is less than said second threshold value.

22. the safety subsystem of claim 21, further comprising:

first monitoring means for detecting errors in the blood oxygen level signal provided by said oximeter;

second monitoring means for detecting errors in the signal provided by said means for measuring the fractional amount of oxygen being delivered to the patient; and means for generating said alarm signal in response to an error being detected by one of said first and second monitoring means.

23. the safety subsystem of claim 22 wherein said first and second monitoring means detect missing values of said respective blood oxygen level signal and said measured fractional amount of oxygen signal as the errors in the respective signals.

24. The safety subsystem of claim 21 further comprising, non-volatile memory means for storing the measured blood oxygen level values provided by said oximeter and the measured fractional amount of oxygen being delivered to the patient.

25. The safety subsystem of claim 24 wherein values representing said preferred fractional amount of oxygen are stored in said non-volatile memory means.

26. A method for adaptively controlling the fractional amount of oxygen delivered to a patient comprising the steps of:

a) measuring the blood hemoglobin saturation in the patient during a plurality of intervals over a given period of time and providing said measured values as an output signal;

b) evaluating each of the measured values of said output signal to identify possibly invalid output signal values;

c) eliminating said identified possibly invalid output signal values from said output signal to produce a processed output signal;

d) adjusting the fractional amount of oxygen delivered to the patient in a sense to minimize any difference between said processed output signal and a predetermined desired blood hemoglobin saturation signal.

27. A method for adaptively controlling the fractional amount of oxygen delivered to a patient comprising the steps of:

a) measuring the blood hemoglobin saturation in the patient during a plurality of intervals over a given period of time and providing said measured values as an output signal;

b) evaluating each of the measured values of said output signal to identify possibly invalid output signal values;

c) eliminating said identified possibly invalid output signal values from said output signal to produce a processed output signal by c1) generating a sequence of valid output signal values by substituting a pseudo value for each of said identified possibly invalid output signal values;

c2) generating a running average of successive values of said sequence of valid output signal values, wherein the instantaneous value of said running average is said pseudo value;

c3) providing said running average as said processed output signal; and d) adjusting the fractional amount of oxygen delivered to the patient in a sense to minimize any difference between said processed output signal and a predetermined desired blood hemoglobin saturation signal.

28. The method of claim 27 wherein step c1) includes the steps of:

monitoring the frequency of occurrence of said identified possibly invalid output signal values; and decreasing the value of said substituted pseudo values in proportion to the frequency of occurrence of said identified possibly invalid output signal values.

* * * * *